United States Patent [19]

Takahashi et al.

[11] Patent Number: 4,916,534
[45] Date of Patent: Apr. 10, 1990

[54] ENDOSCOPE

[75] Inventors: Susumu Takahashi, Kunitachi; Tsutomu Igarashi; Atsushi Miyazaki, both of Hachiouji; Kimihiko Nishioka; Akira Hasegawa, both of Hachiouji; Masahiro Chiba; Koji Takamura, both of Hachiouji, all of Japan

[73] Assignee: Olympus Optical Co., Ltd., Tokyo, Japan

[21] Appl. No.: 187,040

[22] Filed: Apr. 27, 1988

[30] Foreign Application Priority Data

Apr. 28, 1987 [JP] Japan .................. 62-103117
Jul. 29, 1987 [JP] Japan .................. 62-189750
Feb. 16, 1988 [JP] Japan ............... 63-18965[U]

[51] Int. Cl.⁴ ............................ A61B 1/04; A61B 1/06
[52] U.S. Cl. ......................................... 358/98; 128/6; 358/225
[58] Field of Search ....................... 358/98, 225; 128/6

[56] References Cited

U.S. PATENT DOCUMENTS 4,576,147 3/1986 Hashiguchi .................. 128/6
4,615,333 10/1986 Taguchi ........................ 128/6
4,618,884 10/1986 Nagasaki ..................... 358/98
4,697,577 10/1987 Forkner ......................... 128/6

Primary Examiner—Howard W. Britton
Attorney, Agent, or Firm—Cushman, Darby & Cushman

[57] ABSTRACT

In order to enable to sufficiently deflect the viewing direction for a distal end having an end surface substantially perpendicular to the optical axis of an objective optical system and minimize aberrations produced due to the deflecting action, the objective optical system for endoscopes comprises at least one surface designed as a deflecting surface or an eccentric surface on the image side of the surface nearest the object to be observed out of the surfaces of the optical components composing the objective optical system so that the light is refracted at least twice for deflecting the viewing direction. In order to shorten total length and minimize outside diameter of the objective optical system and enable to sufficiently eliminate the infrared light incident from the object, the objective optical system comprises at least one optical component made of a substance absorbing the light having the oscillation frequency of the YAG laser light and interference films reflecting the light having the oscillation frequency of the YAG laser light formed on the cemented surfaces of the optical components and/or the surface of emergence of a rear group designed as a positive lens component.

20 Claims, 14 Drawing Sheets

ENDOSCOPE

BACKGROUND OF THE INVENTION (a) Field of the invention:

The present invention relates to an endoscope, and more specifically an optical system for endoscopes.

(b) Description of the prior art:

In the recent years, there have been increasingly used endoscopes so adapted as to observe object images on TV units while forming object images with solid-state image sensors such as CCD arranged in the distal ends, as well as endoscopes equipped with laser scalpels.

However, since the solid-state image sensors have high sensitivity to the infrared light, the sensors may form object images different from those observed by naked eyes, thereby causing misjudgment of affected parts. Further, since the YAG laser beam having a spectrul component in the infrared region (approximately at 1061 nm) is used as the light source for the laser scalpels, the solid-state image sensors may be overflowed by the intense infrared light when the laser scalpels are operated, thereby whitening the entire screen surfaces (the same phenomenon as that caused by too bright light) and making object images invisible. Furthermore, since the YAG laser emits very intense light, the observer is placed in a very dangerous circumstance when the very intense light is reflected on an object and reaches to the observer's eyes through an observation optical system. Therefore, it is general to weaken the laser, before attaining to the solid-state image sensors and human eyes, by arranging infrared light cut filters at adequate positions in the objective optical systems. The infrared light cut filters are of a type which reduces the infrared light, before attaining to the solid-state image sensors and human eyes, by absorbing the infrared light or another type which reduces the infrared light, before attaining to the solid-state image sensors and human eyes, by reflecting the infrared light. Though the infrared light cut filters generally used have a function to reduce infrared light intensity down to some fractions on the order at the second to third position below decimal point, it is necessary to serially arrange two or more filters at a time when the infrared light intensity is high.

FIG. 1 shows a typical example of the conventional objective optical systems for endoscopes using infrared cut filters. In this drawing, the reference numeral 1 represents an image forming lens, the reference numeral 2 designates a stop arranged in the image forming lens 1, the reference numeral 3 denotes a YAG laser light absorption type of cut filter, the reference numeral 4 represents a YAG light reflection type of interference filter formed on the incidence surface of the YAG light absorption type of cut filter, the reference numeral 5 designates an infrared light absorption type of cut filter, the reference numeral 6 denotes an optical low-pass filter consisting of a quartz plate, etc. These optical members form an objective optical system A for endoscopes. The reference numeral 7 represents a solid-state image sensor having a protective glass 8 bonded to the sensitive surface thereof. The spectroscopic characteristics of the YAG laser light absorption type of cut filter 3, YAG laser light reflection type of interference filter 4 and infrared light absorption type of cut filter 5 are shown in FIG. 2.

Though the objective optical system A having the formation described above is capable of eliminating the infrared light almost completely, said objective optical system A comprises two infrared light absorbing filters 3 and 6 and inevitably has a long total length, thereby making it impossible to solve the essential problem of compact design of the distal end demanded for the endoscopes having small diameters.

In the next place, the objective optical system of the type which reduces the infrared light by reflecting it before attaining to the solid-state image sensor 7 poses a problem that transmittance is not lowered sufficiently due to multiple reflections between the filters when two filters are arranged parallelly and serially in the optical path. Speaking concretely, the light reflected by the second filter is reflected again by the first filter arranged before (on the side of incidence) the second filter, returns again to the second filter and the light partially transmits the second filter, thereby increasing transmission light intensity as compared with that in a case where a single filter is used. Especially, on an assumption that reflection is repeated infinitely between the two filters, total transmittance of the two filters cannot be lower than $\frac{1}{2}$ of the transmittance of the filter having the lower transmittance. Accordingly, the objective optical system of this type cannot eliminate infrared light sufficiently and poses a problem that the infrared light hinders observation and constitutes danger during observation.

Though such a problem is not posed, needless to say, when the absorption type of filters shown in FIG. 1 are used, the absorption type of filters are lower in durability (affected more easily especially by humidity) than the interference film filters. When it is obliged to use the interference film filters or when an endoscope is to be used for medical purposes, it may therefore be convenient to design an objective lens system as an oblique view type. As a conventional objective optical system for endoscopes which deflects the viewing direction by utilizing the refraction, there is known an objective lens system comprising an objective optical system A consisting of a prism 9 arranged in the distal end of an endoscope and an image forming lens 1 and an image guide 10, as shown in FIG. 3A. Though this arrangement is often adopted when deflection angle is within 20°, the entrance surface of the prism 9 inclines to the optical axis O and its exit surface is perpendicular to the optical axis. Accordingly, the light entering to the center of visual field or the center of the entrance end face of the image guide 10, that is, the light progressing along the optical axis O is deflected by a desired angle $\phi$ only with the refraction at the entrance surface 9a of the prism 9 as shown in FIG. 3B. In case of an endoscope using an objective lens system performing deflection by utilizing the refraction by the surface 9a only located on the side nearest the object as in the case of this conventional example, there are posed problems that the distal end of the endoscope must be inclined and that the inclination angle is too large relative to the effect obtained by the deflection. Further, there are posed problems that, when the endoscope is used in water or another medium, the deflection is reduced remarkably as compared with that in air, thereby making it impossible to obtain sufficient deflection of viewing direction, and that the deflecting action produces distortion, astigmatism and chromatic aberration too grave for the deflection effect since the deflection is performed by utilizing refraction on a single surface.

SUMMARY OF THE INVENTION

A primary object of the present invention is to provide an endoscope equipped with an oblique view type of objective optical system having a tip end surface substantially perpendicular to the optical axis, assuring a minimum reduction of visual field deflection even in water, controlling distortion, astigmatism, chromatic aberration, etc. produced due to deflecting action to possible minimum levels respectively, and designed to assure a sufficient deflection angle of viewing direction.

Another object of the present invention is to provide an endoscope equipped with an objective optical system short in total length thereof, having a compact design and capable of sufficiently eliminating infrared light.

A still other object of the present invention is to provide an endoscope equipped with an objective optical system so adapted as to prevent transmittance to be enhanced by multiple reflections and comprising a plural number of infrared light cut filters.

The objective optical system according to the present invention is so adapted as to refract light at least twice for deflecting viewing direction by arranging obliquely or eccentrically, at least one surface except the entrance surface (the first surface) of the optical component closest to an object out of the surfaces of such optical components as lenses, prisms, etc. to compose said objective optical system, to the optical axis. In this case, the entrance surface of the optical component closest to the object may be perpendicular, oblique or eccentric to the optical axis. Whereby, the deflecting function of said first surface is lessened and sufficient deflection of viewing direction is obtained though the distal end surface of the endoscope is substantially perpendicular to the optical axis. Further, the design makes it possible to minimize the reduction of the deflection angle in water and aberrations produced by the deflection.

Further, the objective optical system for endoscopes according to the present invention comprises a front lens group composed by cementing a transparent plate to the incident surface of a plano-convex lens and bonding a stop on the cemented surface, and a rear lens group composed of a positive lens, at least one of the optical components arranged in said front and rear lens groups being made of a substance which absorbs the light having the oscillation frequency of the YAG laser, and interference films which reflects the light having the oscillation frequency of the YAG laser being formed on the cemented surfaces of the optical components arranged in said front and rear lens groups and/or the emerging surface of said rear lens group. This formation makes it possible to sufficiently eliminate the infrared light without reserving substantial filter spaces and design the objective lens system compact by shortening the total length thereof.

These and other objects as well as the features and advantages of the present invention will be apparent from the following detailed description of the preferred embodiments when taken in conjunction with the accompanying drawings.

DESCRIPTION OF THE PREFERRED EMBODIMENTS

Figure 1:
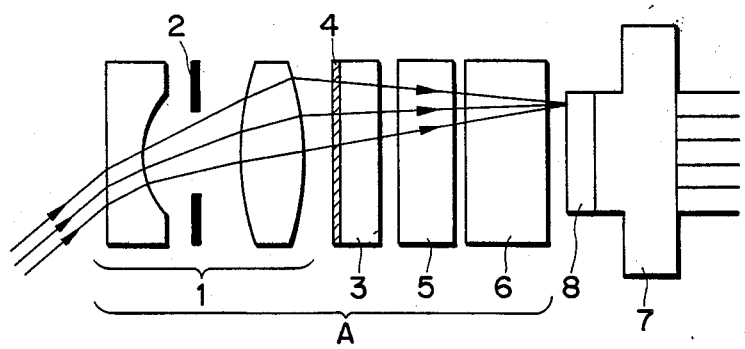
FIG. 1 is a sectional view illustrating an example of the formations of the conventional objective optical systems for endoscopes.

Now, the preferred embodiments of the objective optical system according to the present invention will be detailedly described with reference to the accompanying drawings wherein the members and parts substantially similar to those of the conventional examples are represented by the same reference numerals.

Figure 4A:
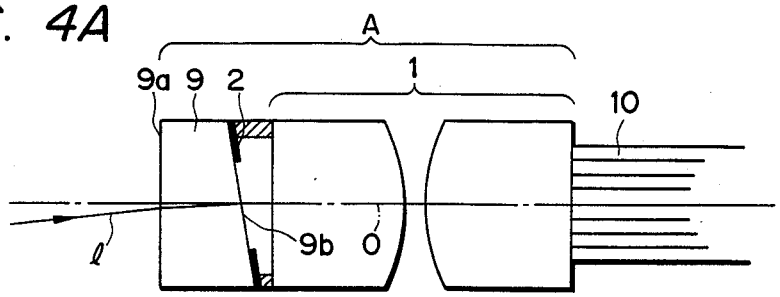
FIGS. 4A and 4B show sectional views illustrating formation of an embodiment of the objective optical systems for endoscopes according to the present invention.

In the first place, the embodiment shown in FIG. 4A is provided with an objective optical system A consisting of an image forming lens 1 arranged before (on the object side) an image guide 10 and a deflecting prism 9 arranged before said image forming lens. In this embodiment, the optical axis of the objective optical system A is coincident with the optical axis of the image guide 10 as shown in FIG. 4A, and these optical axis will hereafter be referred to simply as "the optical axis O" will no distinguishment. The deflecting prism 9 arranged before the image forming lens 1 has a surface $9a$, on the object side, which is a plane perpendicular to the optical axis O and another surface $9b$, on the side of the image forming lens 1, which is a plane having a normal inclined relative to the optical axis. The reference numeral 2 represents a stop.

Figure 4B:
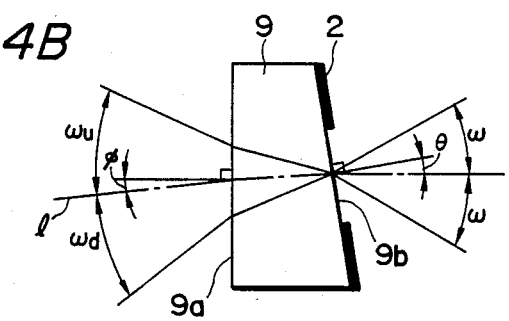

Since this embodiment has the formation described above, the principal ray to be incident on the center of the image guide 10 passes along the optical axis O after having passed through the deflecting prism 9 and angle of incidence of this ray relative to the optical axis O is the angle of deflection of viewing direction. As shown in FIG. 4B, the ray to progress along the optical axis O is refracted by the exit surface $9b$ of the prism 9 and is obliquely intersected to the entrance surface $9a$ in spite of the fact that the surface $9a$ is perpendicular to the optical axis, because the exit surface $9b$ inclines to the optical axis by an angle of $\theta$. As the result, the ray is also refracted by the entrance surface $9a$ to impart a desired angle $\phi$ of deflection. Further, half angle of field $\omega$ determined by the image forming lens 1 is not varied on the plane perpendicular to the plane including the normal of the deflecting surface $9b$ of the prism 9 and the optical axis, but is varied on the plane including the normal and the optical axis by the refractive function of the prism 9. When the half angle of field as seen in the viewing direction on this plane is represented by $\omega_d$ on the side of the deflection from the optical axis and by $\omega_u$ on the opposite side, the deviation of $\omega_u$ from $\omega$ produces distortion due to deflecting action and, in addition, has relation to astigmatism, chromatic aberration, etc. produced depending on degree of the refracting action. As the deviation is larger, aberrations will be more remarkable. When refractive index n of the prism 9 and vertical angle $\theta$ of the surface 9b on the side of the image forming lens are assumed to be 1.883 and 13.42° respectively, relationship between the half angle of field $\omega$ before deflection and the half angles of field $\omega_d$ and $\omega_u$ is as summarized in Table 1 below:

TABLE 1

| $\omega$ | 20° | 30° | 40° | 50° |
|---|---|---|---|---|
| $\omega_d$ | 18.77° | 27.17° | 34.70° | 41.03° |
| $\omega_u$ | 21.21° | 33.20° | 47.29° | 71.84° |

In this case, the deflection angle of viewing direction $\phi$ is 12° in air and a deflection angle of 9° can be reserved even in water since the refracting surfaces are not located only on the object side surface of the prism 9. Further, when the lower principal ray is parallel to the first surface on the object side to form the maximum $\omega_d$, $\omega$ is 50.49° and the optical system is usable up to a maximum angle of field 2$\omega$ around 90°.

Figure 3A:
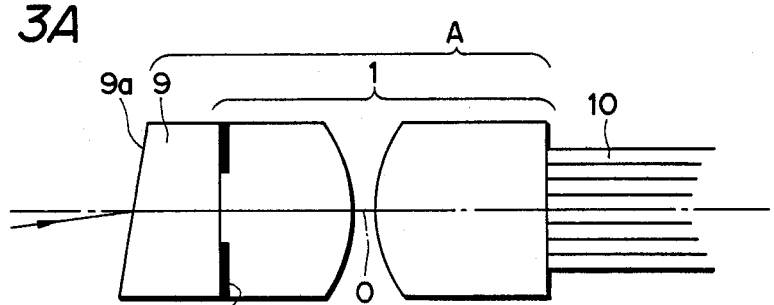
FIGS. 3A and 3B are sectional views illustrating an example of the formations of the conventional oblique view type of objective optical systems for endoscopes.
Figure 3B:
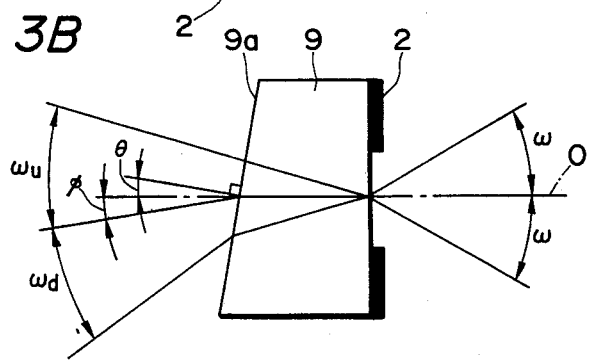

When the conventional example shown in FIGS. 3A and 3B is assumed to have a deflection angle of viewing direction of 12° in air, interrelation among the half angle of field $\omega$ before deflection, and half angles of field $\omega_u$ and $\omega_d$ after deflection is summarized as shown in Table 2.

TABLE 2

| $\omega$ | 20° | 30° | 38° |
|---|---|---|---|
| $\omega_u$ | 20.28° | 29.57° | 36.57° |
| $\omega_d$ | 23.48° | 38.42° | 61.94° |

The prism 9 has a refractive index of 1.883 and the vertical angle is 12.94°. In this case, deflection angle of viewing direction $\phi$ is 5.54° in water and the deflection angle of viewing direction in water is remarkably narrowed since the first surface on the object side only has refracting function. Further, when the lower principal ray is parallel to the first surface on the object side to form a maximum $\omega_d$, $\omega$ is 38.13° and the conventional optical system is usable up to a maximum angle of field 2$\omega$ of about 60°. As is clear from comparison between Table 1 and Table 2, the embodiment shown in FIG. 4A which performs refraction twice for deflecting viewing direction causes smaller the difference between $\omega_u$ and $\omega_d$, produces less aberrations due to deflection of viewing direction and forms better images regardless of the deflection of viewing direction than the conventional example. As is understood from the foregoing descriptions, the embodiment shown in FIG. 4A is an objective optical system for endoscopes comprising an objective lens whose first surface on the object side is perpendicular to the optical axis, capable of keeping the reduction of deflection angle of viewing direction to a minimum in water with no restriction on the form of the distal end of endoscopes, producing minimum aberrations and having a sufficient deflection angle of viewing direction. In addition, it is preferable for obtaining a sufficient deflection angle of viewing direction that the prism 9 should have a vertical angle $\theta$ of at least 3° and a refractive index of at least 1.6. However, too large a vertical angle $\theta$ of the prism 9 will make it impossible to obtain a wide half angle of field $\omega$ and it should preferably be 45° at maximum.

Figure 5:
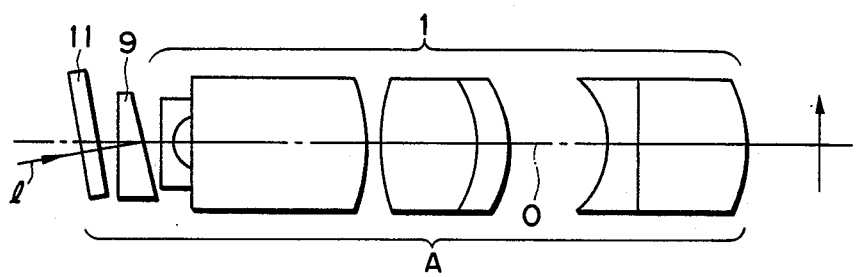
FIG. 5 is a sectional view illustrating the formation wherein a cover glass is arranged on the object side in the embodiment shown in FIG. 4.

FIG. 5 shows an example wherein a cover glass 11 is arranged before the prism 9 so as to correctly face to the prism 9 under inclined state in the viewing direction. This example can provide a deflection angle of viewing direction unvaried even in water since both the surfaces of the cover glass have no refracting action.

Figure 6:
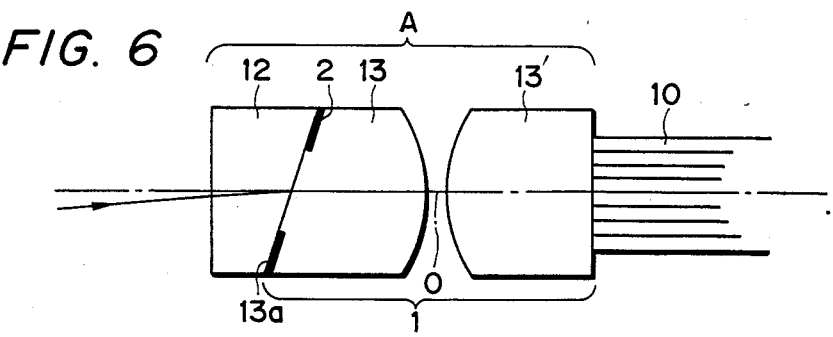
FIGS. 6 through 14 are sectional views illustrating formations of other embodiments different from one another of the objective optical system according to the present invention.

FIG. 6 illustrates a formation of an Embodiment 2 of the present invention. In this embodiment, the surface on the object side of one lens 13 of two positive lenses forming the image forming lens 1 is made as a surface inclined to the optical axis and a prism 12 having an inclined exit surface is cemented on the inclined surface of the positive lens 13 sandwiching a stop 2 therebetween. Deflection of viewing direction is obtained by the inclination of the cemented surface 6a, and difference in refractive index between the prism 12 and the lens 13. When refractive indices of the prism 12 and lens 13 are represented by $n_{12}$ and $n_{13}$ respectively, $n_{12}$ is smaller than $n_{13}$ in the embodiment shown in FIG. 6, but the viewing direction will be deflected reversely when $n_{12}$ is larger than $n_{13}$. This embodiment is characterized in that it can easily correct chromatic aberration. When Abbe's numbers of the prism 12 and lens 13 are represented by $\nu_{12}$ and $\nu_{13}$ respectively, $\nu_{12}$ should be smaller than $\nu_{13}$ for a relation of $n_{12} < n_{13}$ or $\nu_{12}$ should be larger than $\nu_{13}$ for a relation of $n_{12} > n_{13}$. Since the Embodiment 2 requires no spacing tube unlike the Embodiment 1, the former is suited for use in very this endoscopes for blood vessels.

Figure 7:
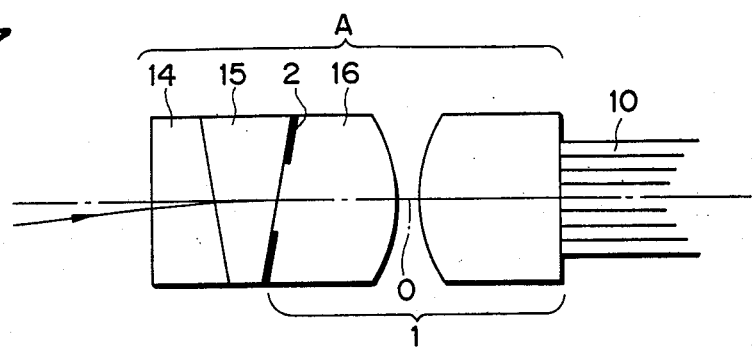

FIG. 7 illustrates a formation of an Embodiment 3 wherein a cemented surface serving for deflection of the viewing direction is added to that in the Embodiment 2 in order to accomplish deflection of viewing direction. Accordingly, less aberrations are produced in the Embodiment 3. Further, this embodiment is capable of correcting chromatic aberration with the cemented surfaces. When refractive indices of the prism 14, prism 15 and lens 16 are represented by $n_{14}$, $n_{15}$ and $n_{16}$ respectively, and Abbe's numbers thereof are designated by $\nu_{14}$, $\nu_{15}$ and $\nu_{16}$ respectively, $\nu_{14} > \nu_{15} < \nu_{16}$ should be selected for $n_{14} > n_{15} < n_{16}$ or $\nu_{14} < \nu_{15} > \nu_{16}$ should be selected for $n_{14} < n_{15} > n_{16}$.

Figure 8:
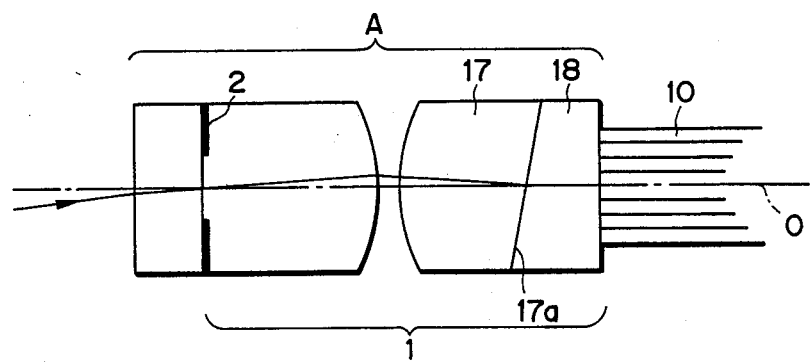

FIG. 8 illustrates a formation of an Embodiment 4 of the present invention wherein a cemented surface 17a inclined relative to the optical axis is arranged in the vicinity of the imaging surface of the image forming lens 1 and the first surface on the object side is perpendicular to the optical axis. Accordingly, refraction for deflecting the viewing direction is performed twice on the first surface on the object side and the cemented surface. For correcting chromatic aberration in this embodiment, $\nu_{17} > \nu_{18}$ should be selected for a relation of $n_{17} < n_{18}$ or $\nu_{17} < \nu_{18}$ should be selected for a relation of $n_{17} < n_{18}$ when refractive indices of the lens 17 and prism 18 are represented by $n_{17}$ and $n_{18}$ respectively, and Abbe's numbers thereof are designated by $\nu_{17}$ and $\nu_{18}$ respectively.

Figure 9:
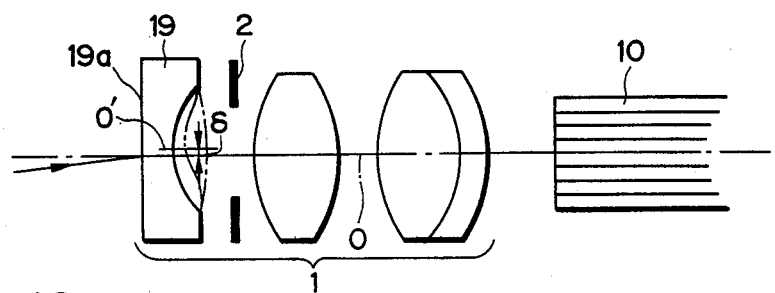

FIG. 9 shows a formation of an Embodiment 5 of the present invention so adapted as to perform deflection of the viewing direction by placing a negative lens 19 arranged on the extreme object side in the image forming lens 1 at a position eccentric by $\delta$. In this embodiment, the light to progress along the optical axis O will pass through the lens 19 in a position out of the optical axis O' of the lens 19. Therefore, though the entrance surface of the lens 19 is perpendicular to the optical axis O, the light is refracted respectively at the entrance and exit surfaces of the lens 19, that is, deflection is performed by twice refraction. The curved surface to be placed at the eccentric position is not limited to a concave surface as adopted in this embodiment, but may be a convex surface as shown in the chain line or an aspherical surface as shown in the two-point chain line.

Figure 10:
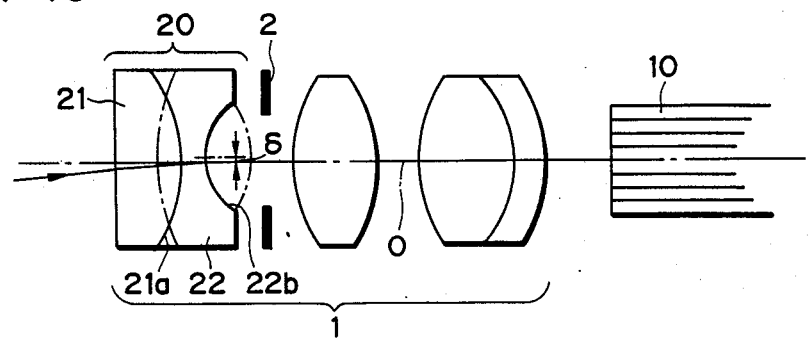

FIG. 10 shows an Embodiment 6 of the present invention wherein the lens component arranged at the position eccentric by δ is designed as a cemented doublet 20. When refractive indices of the lens 21 and lens 22 are represented by $n_{21}$ and $n_{22}$ respectively, $n_{21}$ is larger than $n_{22}$ and the cemented surface is designed as a convex surface.

When the cemented doublet to be placed at the eccentric position is a convex lens as shown in the chain lines, the cemented surface should be designed as a concave surface. In this embodiment, only the image side concave surface 22a of the lens 20 may be placed at an eccentric position as indicated by δ in FIG. 7. In other words, the cemented surface 21a may or may not be eccentric.

Figure 11:
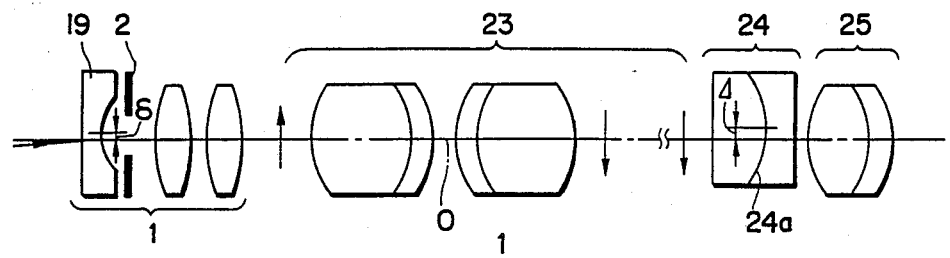

FIG. 11 illustrates an Embodiment 7 of the present invention wherein the viewing direction deflecting means of the afore-mentioned Embodiment 5 is applied to an objective optical system of a non-flexible endoscope. Speaking concretely, a front lens 19 of the objective optical system 1 is eccentric from the optical axis and a cemented doublet 24 having a cemented surface 24a eccentric by Δ from the optical axis is arranged after (on the image side) a relay optical system of the non-flexible endoscope. This embodiment is capable of correcting aberrations produced due to deflection of the viewing direction in the objective optical system by utilizing the high curvature on the cemented surface of the eccentric lens component 24. Further, aberrations can be corrected more favorably by adopting an aspherical surface on the cemented doublet 24. Moreover, this embodiment is capable of correcting aberrations sufficiently with no restriction on outside diameter of the lens arranged in the distal end of the non-flexible endoscope by arranging the aberration correcting lens component 24 after (on the image side) the relay optical system 23. In addition, axially symmetrical aspherical surfaces may be used in the non eccentric optical system, for example, on the objective optical system 1, relay lens system 23 and eyepiece 25.

Figure 12:
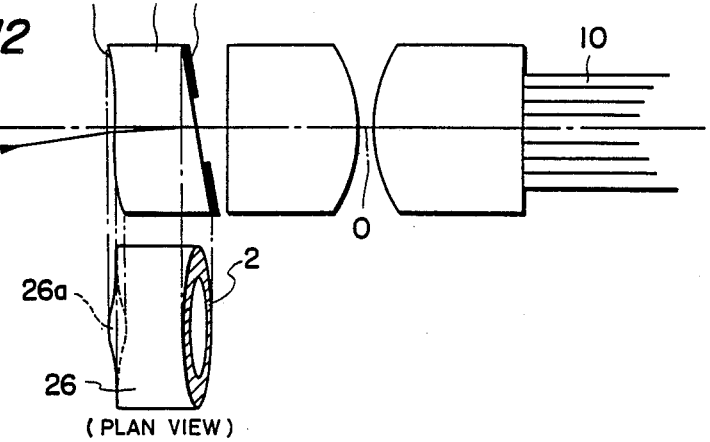

FIG. 12 shows an Embodiment 8 of the present invention wherein the first surface 9a of the prism 9 used in the first embodiment shown in FIG. 4A is designed as an aspherical surface which is not axially symmetrical. Speaking concretely, the prism 26 shown in FIG. 12 has an aspherical surface 26a. The first surface 26a located on the object side is designed as an aspherical surface so as not to increase refractive action abruptly at the periphery of the visual field, thereby preventing aberrations from being produced by the deflection of the viewing direction.

Figure 13:
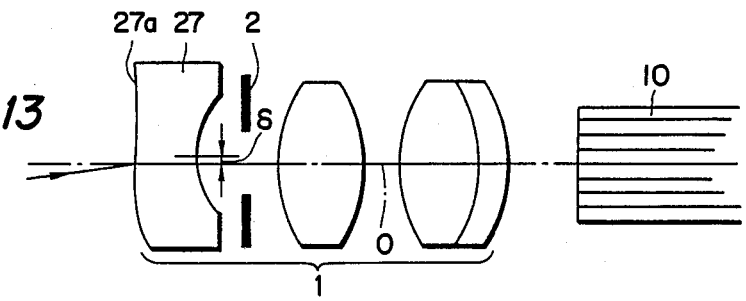

FIG. 13 shows an Embodiment 9 of the present invention wherein the first surface located on the object side in the fifth embodiment shown in FIG. 9 is designed as an aspherical surface for the same reason for the Embodiment 8, and the prism 27 has an aspherical surface 27a which is not axially symmetrical.

The embodiments 8 and 9 (shown in FIGS. 12 and 13 respectively) adopt, as described above, the aspherical first surfaces located on the object side which are not axially symmetrical. These aspherical surfaces have such a shape that a portion near the optical axis is perpendicular to the optical axis, positive curvature is higher at portions closer to the periphery on the deflecting side, i.e., on the lower side in the drawings, whereas negative curvature is higher at portions closer to the periphery on the opposite side, i.e., on the upper side in the drawings. Such a design weakens the refractive action on the principal ray at the periphery of the visual field by the first surfaces located on the object side.

Figure 14:
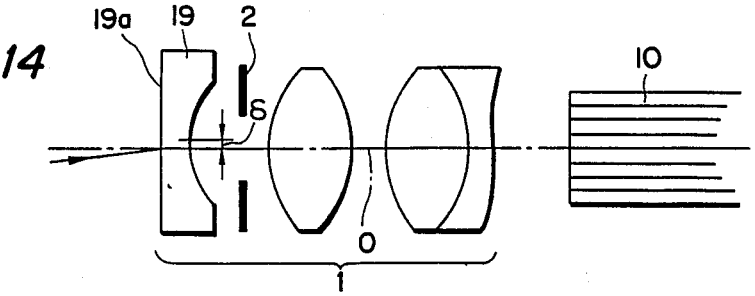

FIG. 14 illustrates an Embodiment 10 of the present invention wherein a surface other than the first surface located on the object side used in the fifth embodiment shown in FIG. 9 is designed as an aspherical surface which is not axially symmetrical. Also in the Embodiment 10, the aspherical surface which is not axially symmetrical can prevent aberrations from being produced by the deflection of the viewing direction. In the Embodiment 10 shown in FIG. 14, the surface of the objective optical system 1 nearest the image guide 10 is designed as an aspherical surface. In addition to the curvature as that of the final surface of the objective optical system, positive curvature is increased at peripherical portions through which peripherical principal ray passes on the deflection side (upper side in the drawing), whereas negative curvature is increased at the peripherical portions, whereby aberrations are corrected and prevented from being produced due to deflection of the viewing direction by producing aberrations which are not axially symmetrical and reverse to the axially asymmetrical aberrations produced by the eccentric concave lens (the lens located on the extreme object side) 19.

As is understood from the foregoing descriptions, the objective optical system for endoscopes according to the present invention has a simple formation, comprises a leading and surface substantially perpendicular to the optical axis, assures little reduction of deflection of the viewing direction, produces little aberration due to the deflection of the viewing direction owing to twice or more refractions for deflection of the viewing direction, and provides a sufficient deflection angle of viewing direction.

Figure 2:
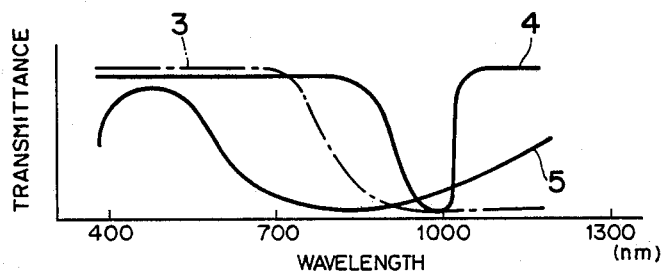
FIG. 2 shows graphs illustrating the spectroscopic characteristics of the various types of filters used in the conventional example shown in FIG. 2.
Figure 15:
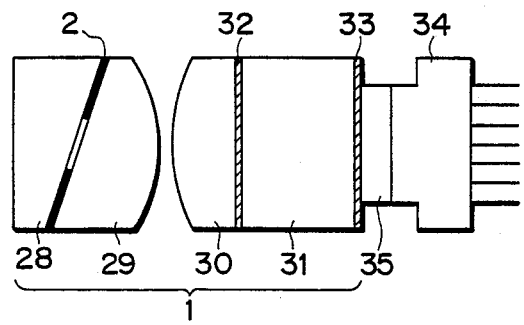
FIGS. 15 through 21, FIGS. 22A and 22B, FIGS. 23 through 28, FIGS. 29A through 29C, FIGS. 30A through 30C, FIGS. 31A and 31B, FIGS. 32 through 40, FIGS. 41A and 41B, and FIGS. 42A and 42B are sectional views illustrating formations of embodiments different from one another of the objective optical system for endoscopes according to the present invention.

FIG. 15 shows an Embodiment 11 of the present invention wherein an objective optical system in which means for cutting the infrared light is added to the objective optical system A shown in FIG. 6 is combined with a solid-state image sensor. In this embodiment, the reference numeral 28 designates a deflecting prism made of a substance absorbing the YAG laser light and also functioning as a YAG laser light cut filter. Before the inclines exit surface of this prism 28 is cemented to a lens 29 corresponding to the front lens 13 of the image forming lens 1 in the embodiment shown in FIG. 6. On the exit side of the lens 29 is arranged a lens 30 corresponding to the rear side lens 13' in the embodiment shown in FIG. 6 and an infrared light absorption type of cut filter 31 having a multi-layer interference film 32, 33 reflecting the YAG laser light on each of the entrance and exit surfaces thereof. The lens 30 and the filter 31 are cemented to each other and a protective glass provided before the surface of a solid-state image sensor 34 is cemented to the exit surface of the filter 31. In addition, spectroscopic characteristics of the YAG laser light absorption type of cut filter 28, YAG laser light reflection type of interference films 32 and 33, and infrared light absorption type of cut filter 31 are the same as those of the filters 3, 4 and 5 respectively shown in FIG. 2. This embodiment is capable of sufficiently eliminating infrared light without substantial filter space since at least one of the optical components in the front group and rear group of the objective optical system is made of a substance absorbing the light having the oscillation frequency of the YAG laser, and interference films reflecting the light having the oscillation frequency of the YAG laser are formed on the cemented surfaces in the front group and rear group and/or the emerging surface in the rear group. Further, the objective optical system is of a compact type as described above. Accordingly, the objective optical system has a short total length and a small outside diameter, and is therefore especially suited for use in endoscopes having small diameters. Furthermore, since the visual sensitivity adjusting infrared absorption type of filter 31 is arranged after the convexo-plane lens 30 used as the rear lens component, i.e., at the position where the principal ray is parallel to the optical axis, this embodiment has an effect to uniformalize color within the visual field. Moreover, since the YAG laser light reflection type of interference films 32 and 33 are formed on both the front and rear surfaces of the infrared light absorption type of cut filter 31, the embodiment has an effect that the lights reflected by the films 32 and 33 are absorbed by the filter 31, thereby preventing flare and ghost light from being produced. In addition, the position of the YAG laser light absorption type of cut prism 28 may be replaced with that of the infrared light absorption type of cut filter 31 in this embodiment. If YAG laser light cut ratio is too low, both the lenses 29 and 30 may be made of substances absorbing the YAG laser light with no influence in the visible range.

Figure 16:
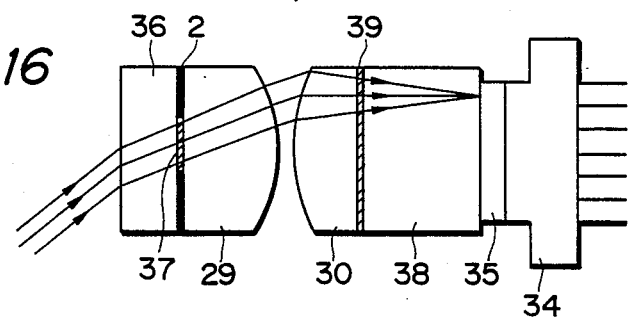

FIG. 16 illustrates an Embodiment 12 of the present invention wherein the reference numeral 36 represents a prism made of a substance absorbing the infrared light, and the reference numeral 37 designates a YAG laser light reflection type of interference filter fitted into the aperture formed by the stop 2 arranged on the cemented surface between the prism 36 and the lens 29. The reference numeral 38 denotes an optical low-pass filter consisting of crystal plate, etc. cemented to the emerging surface of the convexoplane lens 30, and the reference numeral 39 represents a YAG laser light reflection type of interference filter formed on the cemented surface between the convexo-plane lens 30 and the optical low-pass filter 38.

Figure 17:
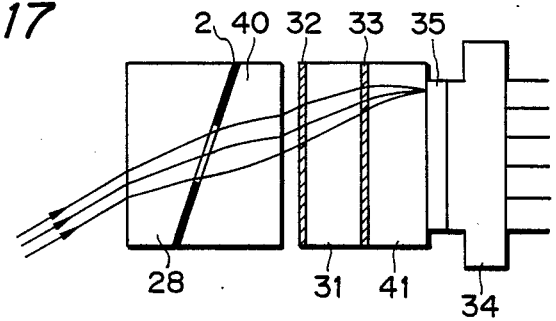

FIG. 17 shows an Embodiment 13 of the present invention wherein radial-gradient refractive index lenses (radial-GRIN lenses) 40 and 41 in which the refractive index is varied from their center portions to their peripheral portions respectively are used in place of the lenses 29 and 30 in the embodiment shown in FIG. 15.

Figure 18:
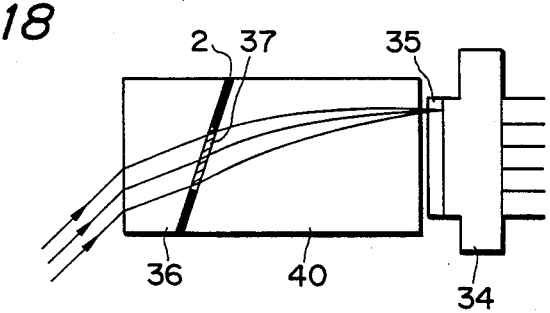

FIG. 18 illustrates an Embodiment 14 of the present invention wherein the entire objective optical system is composed of a single group by cementing an infrared light absorption type of cut prism 36 to the incident surface of the radial-GRIN lens 40, and arranging the stop 2 and YAG laser light reflection type of interference filter 37 on the cemented surface.

Figure 19:
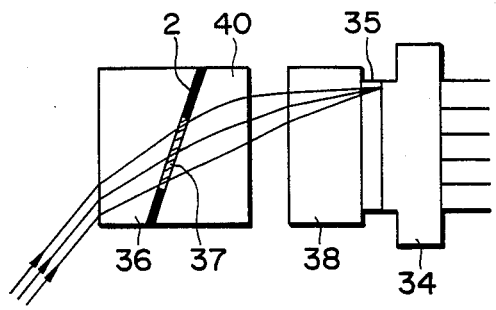

FIG. 19 shows an Embodiment 15 of the present invention which is composed by arranging an optical low-pass filter 38 between the radial-GRIN lens 40 and the protective glass plate 35 for the solid-state image sensor 34 in the embodiment shown in FIG. 18.

In the Embodiments 13 to 15 described above wherein all the surfaces of the optical elements are plane, the YAG laser light reflection type of interference filter may be arranged on any surface, except for the one which is located on the extreme object side.

In addition, since it is possible to preliminarily eliminate infrared light from the illumination light when a dark place is to be illuminated with a self illumination as in the case of an endoscope, the infrared light absorption type of filter may be unnecessary. In such a case, however, it is necessary to arrange a YAG laser light cut filter at a place in contact with the YAG laser light reflection type of interference filter. Further, it is advantageous from the viewpoint of space to design the protective glass plate for the solid-state image sensor as a YAG laser light absorption type of cut filter and to arrange the YAG laser light reflection type of interference filter on the surface of the protective glass plate. Moreover, set position of the solid-state image sensor can be properly adjusted in the Embodiments 11 through 15 by displacing the rear group to which the solid-state image sensor has preliminarily been cemented or displacing only the solid-state image sensor relative to the front and rear groups which have preliminarily been fixed. In these embodiments, infrared light is eliminated efficiently by the objective optical systems having short total lengths and small diameters.

Figure 20:
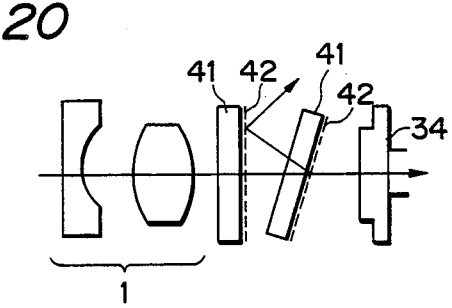

FIG. 20 illustrates an Embodiment 16 of the present invention wherein the reference numeral 41 represents two infrared light cut filters which are composed by evaporationcoating infrared light cutting interference films 42 to sides of plane parallel plates, etc., and arranged in mutually inclined positions between the image forming lens 1 and the image sensor 34. Since the filters 41 are inclined toward each other as described above, the light reflected by the interference film 42 of the second filter 41 is incident on the interference film 42 of the first filter 41 at an angle larger than 0 and accordingly goes out of the optical path rather early without multiple reflections, thereby preventing transmittance from being enhanced. When transmittance of the interference film 42 is represented by $\tau$, the objective optical system has transmittance of $\tau^2$ as a whole and exhibits a high effect for cutting the YAG laser light.

Figure 21:
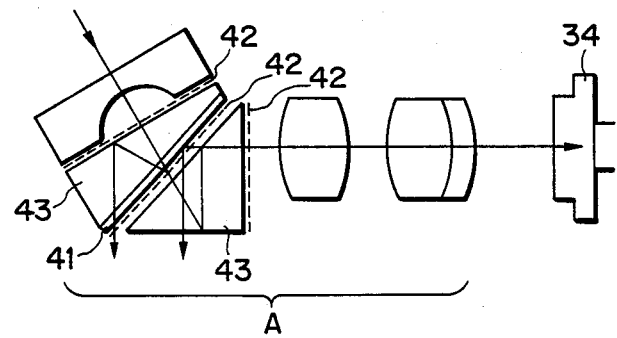

FIG. 21 illustrates an Embodiment 17 of the present invention wherein an infrared light cutting interference film 42 is evaporation-coated on the incident surface or emerging surface of a prism 43 (having a surface perpendicular to the optical axis and a surface not perpendicular to the optical axis) in the objective optical system A for oblique view. This embodiment has merits of simple formation and narrow space to be occupied, since it requires only evaporation-coating of the infrared light cutting interference film 42 to the entrance surface or exit surface of the prism 43.

Figure 22A:
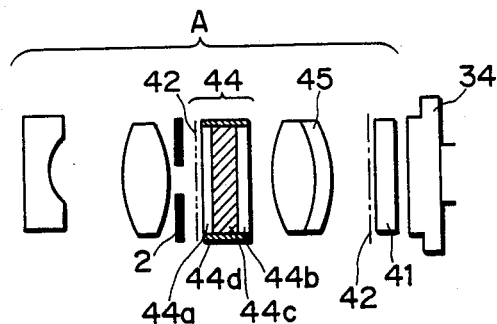
Figure 22B:
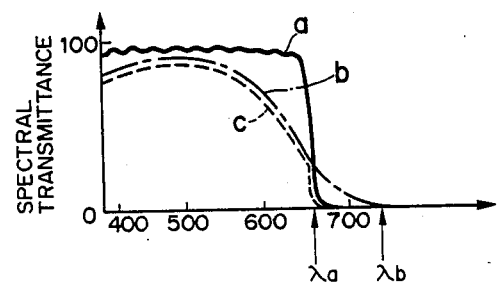

FIG. 22A shows an Embodiment 18 of the present invention wherein a lens 45 is arranged between a composite filter 44 and an infrared light cut filter 41, said composite filter being composed by sandwiching and cementing an infrared light absorbing filter 44c between a plane parallel plate 44a having a front surface evaporation-coated with an infrared light cutting interference film 42 and a plane parallel plate 44b having a rear surface coated with multiple layers, whereas said infrared light cut filter being arranged before the solid-state image sensor 34 and composed by evaporation-coating the front surface thereof with an interference film 42. In this embodiment wherein the light reflected by the interference film 42 of the filter 41 is incident on the filter 44 at an angle larger than 0 owing to the function of the lens 45 though the filters 44 and 41 are parallel to each other and perpendicular to the optical axis, said reflection light goes out of the optical path rather early without multiple reflections, thereby preventing transmittance from being enhanced. Further, since this embodiment comprises the infrared light absorbing filter 44c between the two interference films 42, it is capable of eliminating infrared light more effectively owing to the infrared light absorption by the infrared light absorbing filter 44c. Furthermore, when the infrared light absorbing filter is used in combination with the infrared light cutting interference filter as described above, it is possible to obtain an optical system having high color reproducibility by utilizing the transmittance characteristics of the respective filters. Shown in FIG. 22B are spectroscopic characteristic curves a, b and c of the interference film 42, the infrared absorbing filter 44c and the composite filter 44 composed of a combination thereof. By selecting the infrared light cut wavelengths $\lambda_a$ and $\lambda_b$ indicated on the characteristic curves a and b so as to obtain a relation of $\lambda_a \leq \lambda_b$, color reproducibility is improved since transmittance varies gradually at wavelengths shorter than $\lambda_a$ and abruptly at wavelengths longer than $\lambda_a$.

Figure 23:
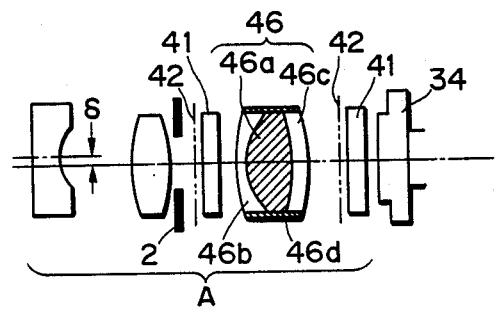

FIG. 23 illustrates an Embodiment 19 of the present invention wherein in the objective optical system A, two infrared light cut filters 41 are arranged on both the sides of a lens 46 which is composed by cementing a lens-like infrared light absorbing filter 46b between two lenses 46a and 46c, and by coating the side surfaces thereof with a black paint 46d. This embodiment has the same effect as the embodiment shown in FIG. 22A and, in addition, the merit of the cemented lens which is capable of correcting coma, spherical aberration, chromatic aberration, etc. at the same time.

Figure 24:
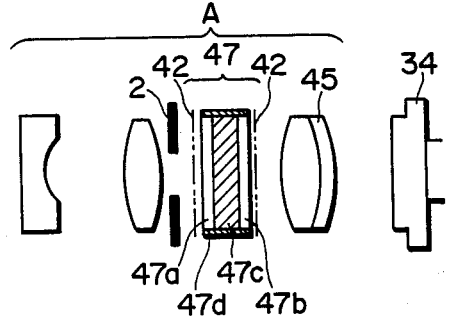

FIG. 24 shows an Embodiment 20 of the present invention wherein, in the objective optical system A, arranged before a lens 45 is a composite filter 47 which is composed by sandwiching and cementing an infrared light absorbing filter 47c between a plane parallel plate 47a having an interference film 42 evaporation-coated to the front surface thereof and a plane parallel plate 47b having an interference film 42 evaporation-coated to the rear surface thereof, and coating the side surfaces thereof with a black paint 47d. In this embodiment, the multiple reflection is prevented by absorbing the YAG laser light with the infrared light absorbing filter 47c arranged between both the interference films 42. Though it is preferable for the infrared light absorbing filter 47c to have transmittance below 30%, the transmittance is ordinarily set on the order of 10% so as not to lower transmittance for the visible light excessively since transmittance for the visible light is generally lowered by lowering transmittance for the infrared light. This embodiment provides a merit to allow to design the composite filter compact.

Figure 25:
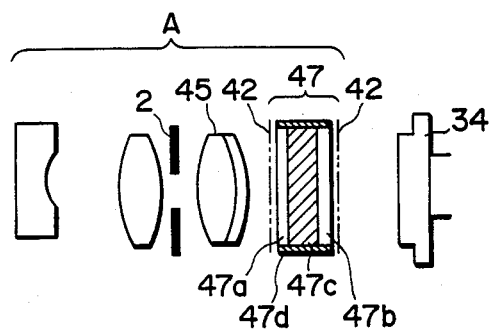

FIG. 25 illustrates an Embodiment 21 of the present invention wherein the composite filter 47 is arranged between the lens 45 and the solid-state image sensor 34 unlike the Embodiment 20 described above. In case of the Embodiment 21 wherein angle of incidence is apt to be large on the interference film 42 due to the function of the lens 45 and the infrared light cutting efficiency of the interference film 42 varies depending on angle of incidence, it is necessary to design the optical system so as to obtain a predetermined angle of incidence, and it is ordinarily set at 30° or narrower. This embodiment also has a merit to allow to design the composite filter compact.

Figure 26:
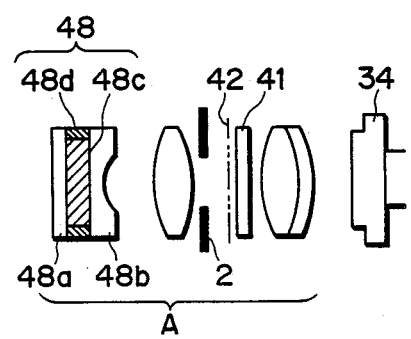

FIG. 26 shows an Embodiment 22 of the present invention wherein arranged in the front most section of the objective optical system A is a composite filter 48 which is composed by cementing an infrared light absorbing filter 48 having smaller diameter between a plane parallel plate 48a and a plano-convex lens 48b, and by coating the side surfaces thereof with a black paint 48d. Since this embodiment comprises the infrared light absorbing filter 48c having a diameter smaller than those of the plane parallel plate 48a and the plano-convex lens 48b, it permits thickening the black paint 48d and has a high moisture-preventive effect.

Figure 27:
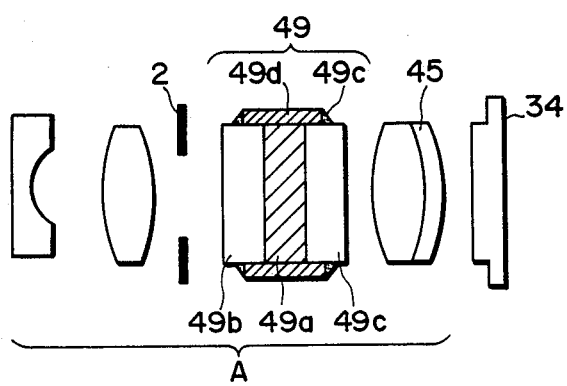

FIG. 27 illustrates an Embodiment 23 of the present invention wherein arranged in the objective optical system A is a filter 49 which is composed by attaching cover glass plates 49b and 49c to both surfaces of an infrared light absorbing glass plate 49a, fitting a metallic protective frame 49d so as to cover at least the circumferential surface of the infrared light absorbing glass plate 49a, and charging the corners formed between the end surfaces of said protective frame 49d and cover glass plates 49b and 49c with a filling material 49e having low hygroscopicity. This embodiment has merits that moisture resistance of the infrared light absorbing glass plate 49a is enhanced by the metallic protective frame 49d, and that the filling material can easily be charged and enhances working efficiency.

Figure 28:
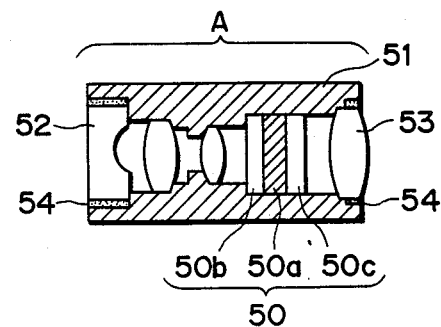
Figure 29A:
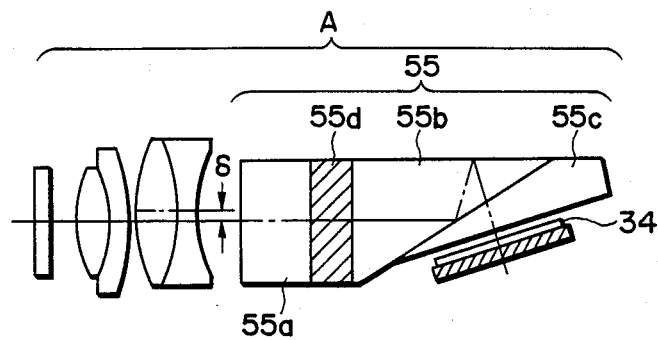
Figure 29B:
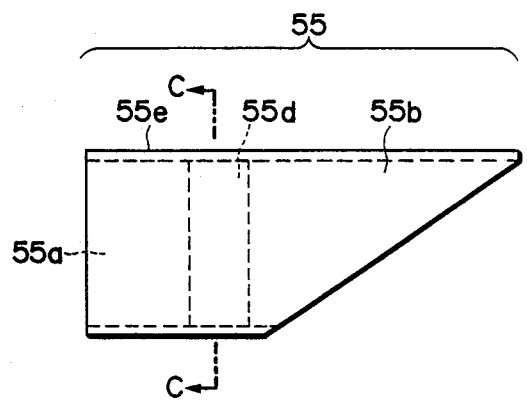
Figure 29C:
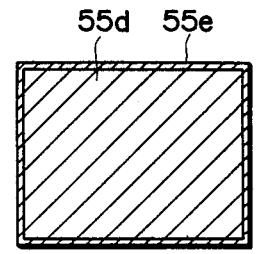

FIG. 28 shows an Embodiment 24 of the present invention wherein the objective optical system A as a whole including a filter 50 composed by attaching cover glass plates 50b and 50c to both surfaces of an infrared light absorbing glass plate 50a is fixed in a metallic lens frame 51, and a filling material 54 is charged between the frontmost lens 52 and lens frame 51 and between the rearmost lens 53 and the lens frame 51 respectively. The embodiment has merits that moisture resistance of the infrared light absorbing glass plate 55a is enhanced and that outside diameter of the optical system is not enlarged In addition, the cover glass plates 55b and 55c may or may not be attached FIGS. 29A through 29C illustrates an Embodiment 25 of the present invention. FIG. 29A shows a general view, FIG. 29B presents a side view of main parts on an enlarged scale and FIG. 29C illustrates a sectional view taken along the C—C line in FIG. 29B. Arranged in the objective optical system A is a composite filter 55 which is composed by fitting an infrared light absorbing filter 55d between a crystal filter 55a for eliminating Moire, false color, etc and prisms 55b and 55c for enabling oblique arrangement of the solid-state image sensor 34, bonding the cementing surfaces thereof with an optical bonding agent and coating the circumferential surfaces thereof entirely with a moisture preventive paint 55e. Though the infrared light absorbing filter 55d has high moisture resistance in this embodiment, a higher moisture preventive effect can be obtained by mixing a small amount of moisture absorbing agent in the optical bonding agent so that moisture remaining on the surfaces of the optical components at the bonding stage is absorbed by the moisture absorbing agent.

Figure 30A:
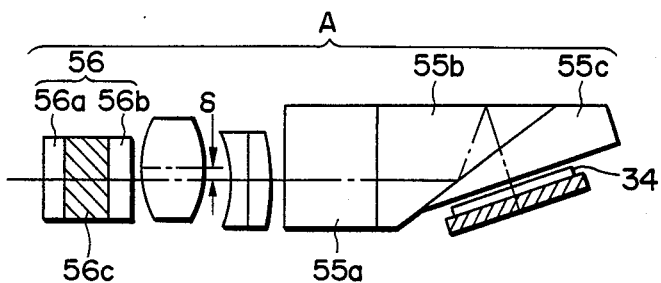
Figure 30B:
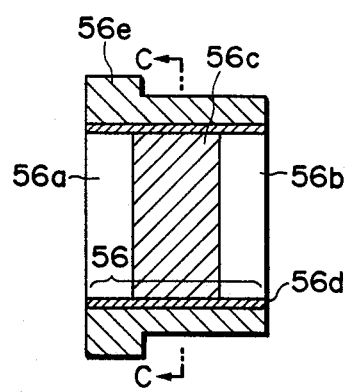
Figure 30C:
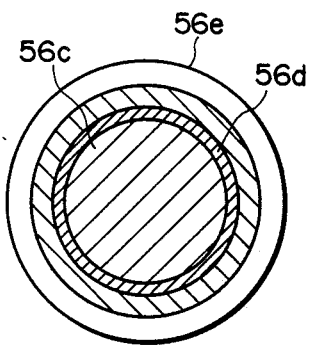

FIGS. 30A through 30C illustrates an Embodiment 26 of the present invention. FIG. 30A shows a general view, FIG. 30B presents a sectional view of main parts on an enlarged scale and FIG. 30C illustrates a sectional view taken along the C—C line in FIG. 30B. Arranged in the objective optical system A is a cover glass member 56 which is composed by fitting an infrared light absorbing filter 56c between optical glass plates 56a and 56b, bonding the cementing surfaces thereof with an optical bonding agent, coating all the circumferential surfaces thereof with a moisture preventing paint 56d, surrounding the entire circumference of said cover glass member 56 with a frame 56e and bonding said frame to said cover glass member. Though the infrared light absorbing filter 56c has high moisture resistance also in this embodiment, a higher moisture preventive effect can be obtained by mixing a moisture absorbing agent in the optical bonding agent in the same manner as in the Embodiment 29.

Figure 31A:
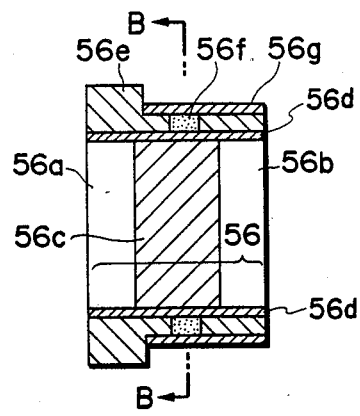
Figure 31B:
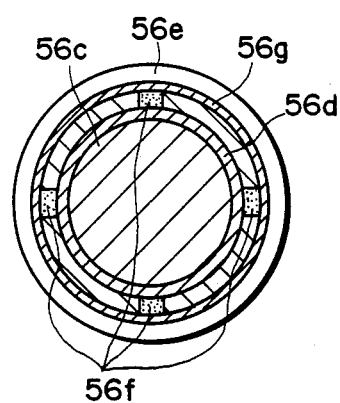

FIGS. 31A and 31B show an Embodiment 27 of the present invention. FIG. 31A illustrates a sectional view of main members and FIG. 31B shows a sectional view taken along the B—B line in FIG. 31A. This embodiment shows a example modified the moisture resistance structure of the infrared light absorbing filter 56c in the Embodiment 26, and FIG. 31A corresponds to FIG. 30B and FIG. 31B to FIG. 30C respectively. That is, this embodiment is so adapted as to eliminate moisture penetrating between the cover glass member 56 and the frame 56e and provides improved moisture resistance by forming a plural number of holes in the outer circumference of the frame 56e, filling the holes with a moisture absorbing agent 56f, surrounding the frame 56e with a pipe 56g and bonding said pipe to said frame.

Figure 32:
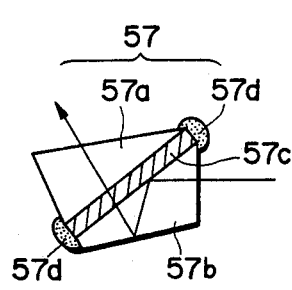

FIG. 32 shows an Embodiment 28 of the present invention wherein arranged in the objective optical system A for oblique view shown in FIG. 21 is a composite filter 57 which is composed by fitting an infrared light absorbing filter 57c between prisms 57a and 57b, bonding the cementing surfaces thereof with an optical bonding agent and coating the side surfaces thereof with a moisture preventive agent 57d.

Figure 33:
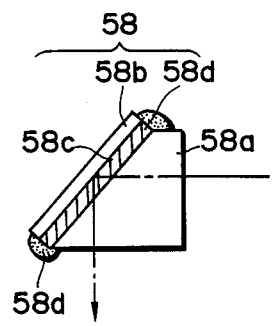

FIG. 33 illustrates an embodiment 29 of the present invention wherein arranged in an objective optical system for side view (not shown) is a composite filter 58 which is composed by fitting an infrared light absorbing filter 58c between a prism 58a and a glass plate 58b, bonding the cementing surfaces thereof with an optical bonding agent and coating the side surfaces thereof with a moisture preventive agent 58d. This embodiment has a merit that the infrared light absorbing filter 58c can be half as thick as the ordinary infrared light absorbing filter since infrared light passes twice through the infrared light absorbing filter 58c at each of the incidence and reflection stages.

Figure 34:
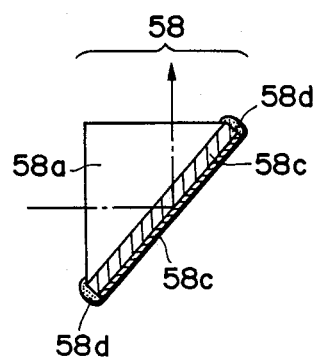

FIG. 34 shows an Embodiment 30 of the present invention as an applicational example of the embodiment shown in FIG. 33. In this embodiment, a moisture preventive structure is composed by arranging a reflection layer 58d in place of the glass plate 58b used in the embodiment of FIG. 33.

Figure 35:
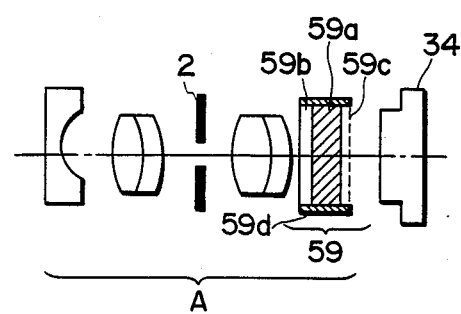

FIG. 35 illustrates an Embodiment 31 of the present invention wherein arranged in the objective optical system A is a composite filter 59 which is composed by bonding a cover glass plate 59b to the front surface of an infrared light absorbing filter 59a, bonding an interference film 59c to the rear surface of said infrared light absorbing filter and coating the circumferential surface thereof with a moisture preventive paint 59d. This embodiment provides enhanced moisture resistance since the interference film 59c has layers in a number larger than that of the ordinary multiple coats. Further, this embodiment is advantageous for preventing flare since the light reflected by the interference film 59c is absorbed by the infrared light absorbing filter 59a.

Figure 36:
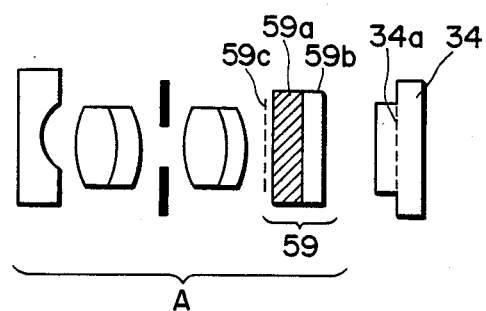

FIG. 36 illustrated an Embodiment 32 of the present invention wherein said composite filter 59 is arranged in the direction opposite to that in the embodiment shown in FIG. 35 in the objective optical system A for an electronic endoscope using a solid-state image sensor equipped with an interference film type of mosaic filter 34a. This embodiment is advantageous for preventing flare since the light reflected by the surface of the mosaic filter 34a is absorbed by the infrared light absorbing filter 59a.

Figure 37:
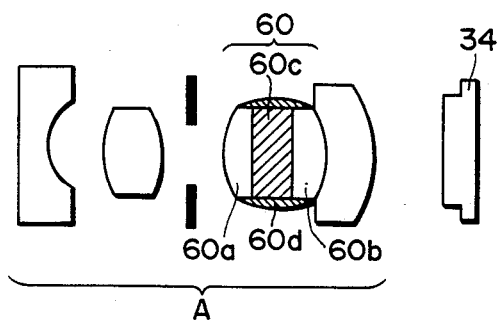

FIG. 37 shows an Embodiment 33 of the present invention wherein arranged in the objective optical system A is a cemented lens component 60 which is composed by sandwiching and cementing an infrared light absorbing filter 60c between lenses 60a and 60b having small diameters, and coating the circumferential surfaces thereof with a moisture preventive paint 60d. This embodiment has a merit to enhance moisture resistance of the infrared light absorbing filter 60c since the lenses 60a and 60b have small diameters and allow to coat the moisture preventive paint in a large amount.

Figure 38:
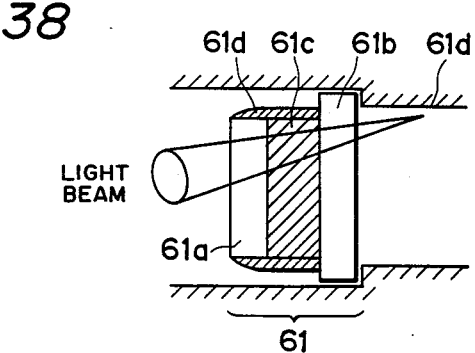

FIG. 38 shows an Embodiment 34 of the present invention wherein arranged in an objective optical system (not shown) is a filter 61 which is composed by sandwiching and cementing an infrared light absorbing filter 61c between cover glass plates 61a and 61b having different diameters, and coating the circumferential surfaces thereof with a moisture preventing agent 61d. This embodiment has a merit that the light cannot be eclipsed even when it is high since the cover glass plate 61b has a diameter larger than that of the cover glass plate 61a. Further, when a frame 61e is used for holding the filter 61 as shown in the drawing, it holds only the surface of the cover glass plate 61b having the larger diameter while avoiding the circumferential surface of the moisture preventive agent having indefinite diameter, thereby minimizing inclination or eccentricity of the filter 61 and assuring high manufacturing precision.

Figure 39:
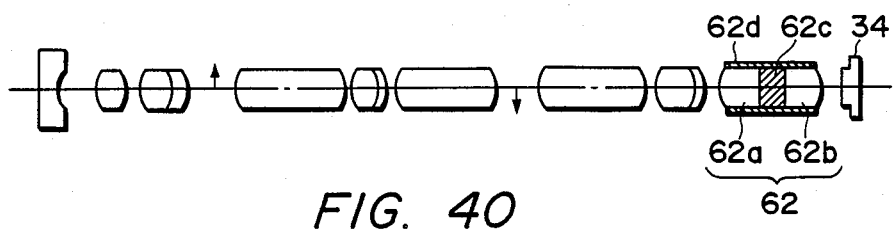

FIG. 39 illustrates an Embodiment 35 of the present invention arranged in a lens system for a non-flexible endoscope is a filter 62 which is composed by sandwiching and cementing an infrared light absorbing filter 62c between lenses 62a and 62b, and costing the circumferences thereof with a moisture preventive agent 62d. In addition, moisture can be further enhanced by fixing a frame around the circumferential surface of the filter 62.

Figure 40:
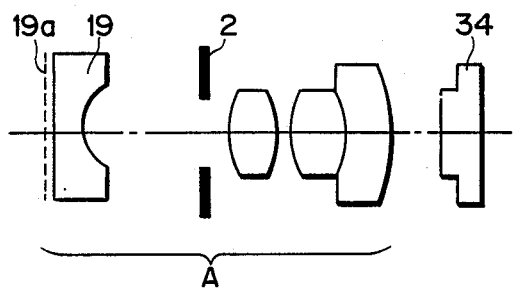

FIG. 40 illustrates an Embodiment 36 of the present invention wherein an interference film 19a is coated on the front surface of the frontmost lens 19. Owing to the interference film 19a formed on the frontmost surface in the optical system, this embodiment comprises few members reflecting light before the interference film 19a and has a merit to minimize multiple reflections. However, this embodiment is suited for cases where difference in angle of incidence is small or the interference film 19a can hardly be injured.

Figure 41A:
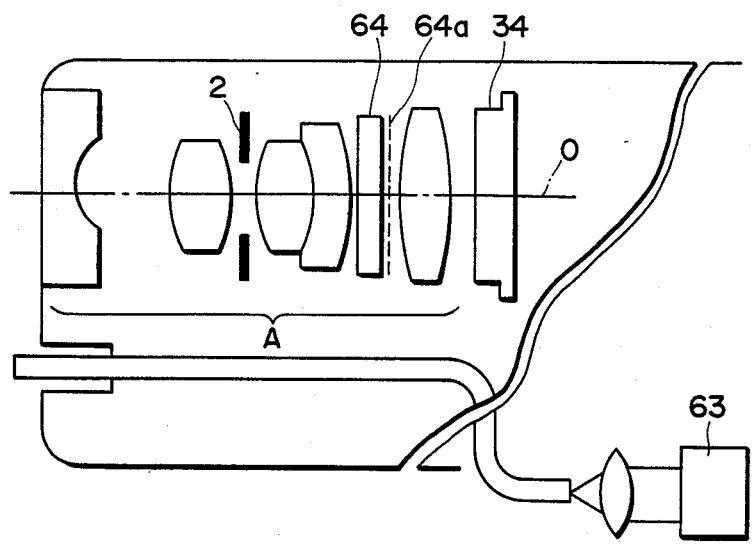
Figure 41B:
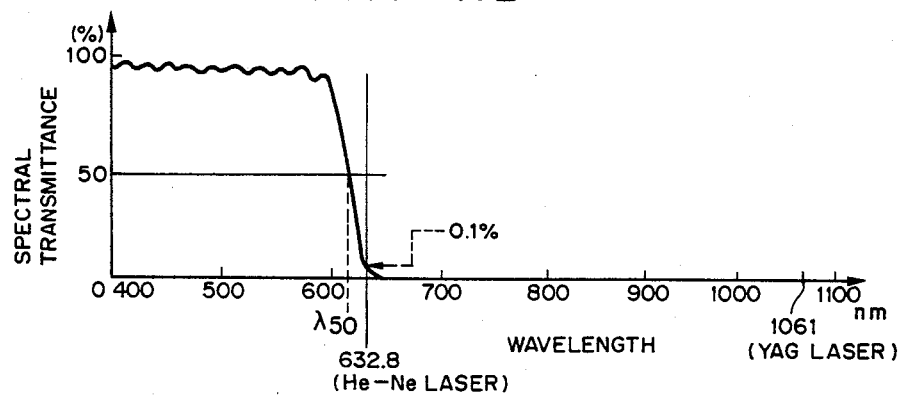

FIGS. 41A and 41B show an Embodiment 37 of the present invention. FIG. 41A illustrates a general view and FIG. 41B is a graph visualizing spectroscopic transmittance characteristic of the infrared light cut filter used in this embodiment. In an electronic endoscope equipped, in addition to YAG laser, with a laser source emitting He-Ne laser light for using the He-Ne laser as the guide light for the YAG laser, this embodiment arranges, in the objective optical system A, an infrared light cut filter 64 composed by evaporation-coating a plane parallel plate, etc. with an interference film 64a. In this case, spectroscopic transmittance characteristic of the infrared light cut filter can be optimized as follows. In order to make the He-Ne laser light (having a wavelength of 632.8 nm) visible, it is sufficient to design the infrared light cut filter 64 so as to have transmittance higher than 0.1% at the wavelength or satisfy $\tau_{632.8} > 0.1\%$. For practical use, however, the lower limit should be set at about 10% and the infrared light cut filter should be designed so as to satisfy $\tau_{632.8} > 10\%$. From another viewpoint, when the infrared light cut filter is designed so as to have transmittance of 50% at a wavelength longer than 610 nm or satisfy $\lambda_{50} > 610$ nm, it should have almost satisfactory transmittance (0.1%) at 632.8 nm. In this case, however, the infrared light cut filter satisfying $\lambda_{50} > 610$ nm is not perfectly free from the fear of too low transmittance at $\lambda = 632.8$ nm when transmittance errors of individual filters are taken into consideration. Therefore, the He-Ne laser light is clearly visibly by designing the infrared light cut filter so as to satisfy $\lambda_{50} > 632.8$ nm or 640 nm, i.e. have transmittance of 50% at 632.8 nm. However, the infrared light cut filter should be designed so as to satisfy also 700 nm $> \lambda_{50}$ or more preferably 670 nm $\geq \lambda_{50}$ since too long $\lambda_{50}$ will lower infrared light cutting efficiently and degrade color reproducibility for TV cameras.

Figure 42A:
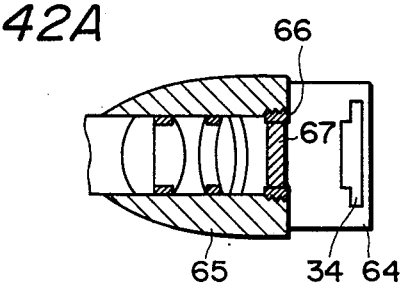
Figure 42B:
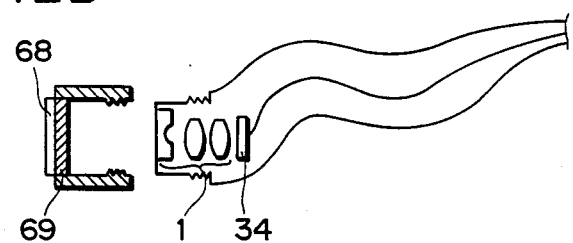

FIGS. 42A and 42B show an Embodiment 38 of the present invention which is so adapted as to allow easy attachment and detachment of an infrared light absorbing filter so that it can be replaced when its characteristic is degraded. FIG. 42A shows an infrared light absorbing filter 67 held in a threaded frame 66 and detachably screwed in an adapter for an endoscope which is externally equipped with a TV camera 64. In this case, it is possible to arrange a plural number of infrared light absorbing filters in a turret so that a deteriorated filter can be switched to another by turning the turret. Further, FIG. 42B illustrates an infrared light absorbing filter 69 integral with a cover glass plate 68 detachably screwed in a distal end of an endoscope, especially in an industrial electronic endoscope.

The present invention is, needless to say, applicable to the cases where electronic endoscopes are equipped not only with infrared light cut filters, but also color temperature varying filters, double refraction filters and/or low-pass filters. Further, the present invention is applicable also for cutting not only the YAG laser light, but also other types of lasers used as non-observation light and non-guide light.

What is claimed is:

1. An endoscope having an objective optical system comprising:
   a plurality of optical components disposed between an object to be observed and a predetermined imaging plane, for forming an image of the object to be observed on said predetermined imaging plane, each said optical component having an entrance surface and an exit surface, at least one of said entrance and exit surfaces of said plurality of optical components, other than the entrance surface of an optical component nearest the object to be observed, being a planar surface inclined relative to an optical axis of said objective optical system and at least one of the immediately preceding and next following surfaces from said one surface of said plurality of components which is being defined in a plane inclined with respect to said one surface.

2. An endoscope as in claim 1, wherein the entrance surface of the optical component nearest the object is aspherical.

3. An endoscope as in claim 1, wherein at least two of said entrance and exit surfaces are defined in a plane inclined with respect to said optical axis.

4. An endoscope according to claim 1 or 3 wherein at least one of said optical components is made of a substance absorbing the light having the oscillation wavelength of the YAG laser light, and an interference film is formed on at least one of cemented surfaces of said optical components and the surface nearest an image to be formed by said objective optical system.

5. An endoscope according to claim 1 or 3 further comprising a light source emitting light having a spectral component at least at a wavelength outside the visible region, a light leading means for irradiating an object with the light from said light source, a solid-state image sensor for receiving the light from the object by way of said objective optical system, and at least two filters composed of multiple-layer interference films for eliminating said spectral component, said filters being arranged in the optical path from said light source through said object and objective optical system to said solid-state image sensor and inclined relative to the optical axis.

6. An endoscope as in claim 1, wherein said optical components include a lens component which has a surface inclined relative to said optical axis and cemented to a correspondingly inclined surface of a next adjacent lens component.

7. An endoscope as in claim 1 or 6, wherein said entrance surface of the optical component nearest the object to be observed is defined in a plane perpendicular to the optical axis.

8. An endoscope as in claim 1, wherein said optical components include an image forming lens and a first prism element disposed between the object to be observed and the image forming lens means, said first prism element having a surface defined in a plane perpendicular to the optical axis of the objective optical system and a surface defined in a plane inclined relative to the optical axis.

9. An endoscope as in claim 8, wherein said plurality of optical components further includes a cover glass disposed between the first prism element and the object to be observed, said cover glass having entrance and exit surfaces defined in planes which are inclined relative to said optical axis and parallel to said inclined plane of said first prism element.

10. An endoscope as in claim 8, including an infrared light cutting interference film evaporation-coated on one of an entrance surface and an exit surface of said first prism element.

11. An endoscope as in claim 8, wherein the entrance surface of said first prism element is defined in a plane perpendicular to the optical axis of the system and the exit surface is defined in a plane inclined relative to the optical axis.

12. An endoscope as in claim 8, wherein said optical components further include a second prism element disposed between an exit surface of said first prism element and said image forming lens means, said second prism element having an entrance surface and an exit surface each defined in planes disposed so as to be inclined relative to said optical axis.

13. An endoscope as in claim 12, wherein said second prism element is cemented to said first prism element and to said image forming lens means.

14. An endoscope as in claim 8, wherein said image forming lens means includes first and second positive lenses.

15. An endoscope as in claim 14, wherein the inclined exit surface of said first prism element is adhered to a correspondingly inclined entrance surface of a said positive lens of said image forming lens means.

16. An endoscope as in claim 15, further comprising a stop sandwiched between said inclined surface of said first prism element and said inclined surface of said image forming lens means.

17. An endoscope in which at least one surface of the surfaces on the image side of the optical components composing an objective optical system is inclined to the optical axis of said objective optical system, at least one of said optical components being made of a substance absorbing light having the oscillation wavelength of YAG laser light, and an interference film being formed on at least one of a cemented surface of said optical components and a surface nearest an image to be formed by said objective optical system.

18. An endoscope according to claim 17 further comprising a light source emitting light having a spectral component at least at a wavelength outside the visible region, a light leading means for irradiating an object with the light from said light source, a solid-state image sensor for receiving the light from the object by weight of said objective optical system, and at least two filters composed of multiple-layer interference films for eliminating said spectral component, said filters being arranged in the optical path from said light source through said object and objective optical system to said solid-state image sensor and inclined relative to the optical axis.

19. An endoscope an endoscope comprising at least one eccentric surface having refracting action on the image side of the surface nearest the object to be observed out of the surfaces of the optical components composing an objective optical system, at least one of said optical components being made of a substance absorbing light having the oscillation wavelength of YAG laser light, and an interference film being formed on at least one of a cemented surface of said optical components and a surface nearest an image to be formed by said objective optical system.

20. An endoscope according to claim 19 further comprising a light source emitting light having a spectral component at least at a wavelength outside the visible region, a light leading means for irradiating an object with the light from said light source, a solid-state image sensor for receiving the light from the object by way of said objective optical system, and at least two filters composed of multiple-layer interference films for eliminating said spectral component, said filters being arranged in the optical path from said light source through said object and objective optical system to said solid-state image sensor and inclined relative to the optical axis.

* * * * *